Figure 1:
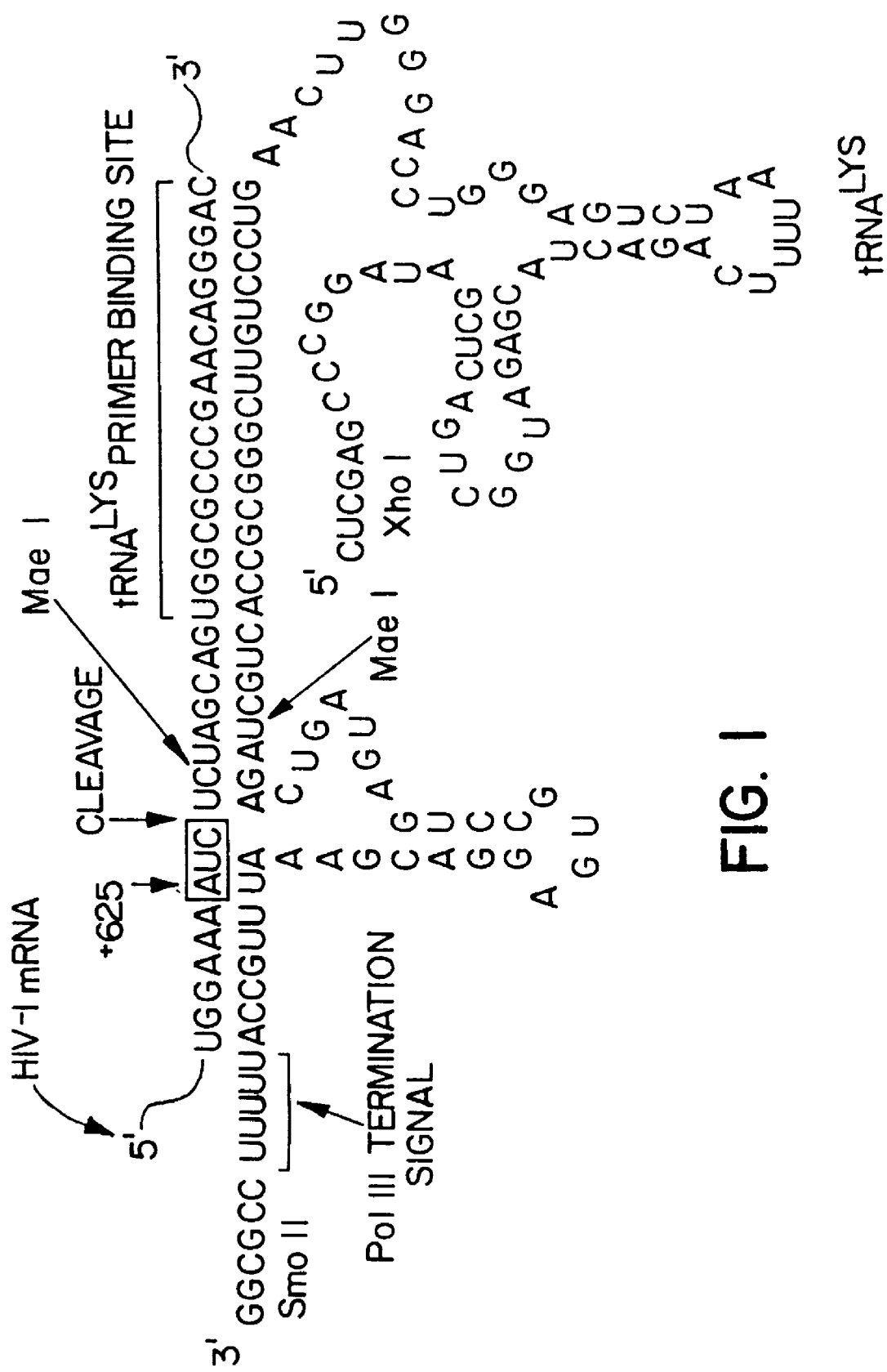

United States Patent [19]
Rossi et al.

[11] Patent Number: 5,827,935
[45] Date of Patent: Oct. 27, 1998

[54] CHIMERIC TRNA$^{LYS}$-RIBOZYME MOLECULES

[75] Inventors: John J. Rossi, Glendora; Garry P. Larson, San Dimas, both of Calif.

[73] Assignee: City of Hope, Duarte, Calif.

[21] Appl. No.: 185,827

[22] PCT Filed: May 27, 1992

[86] PCT No.: PCT/US92/04362

§ 371 Date: Jan. 24, 1994

§ 102(e) Date: Jan. 24, 1994

[87] PCT Pub. No.: WO93/24133

PCT Pub. Date: Dec. 9, 1993

[30] Foreign Application Priority Data

May 27, 1992 [WO] WIPO ............... PCT/US92/04362

[51] Int. Cl.$^6$ ............... C12N 15/11; C07H 21/04; C12Q 1/68
[52] U.S. Cl. ............... 536/23.1; 536/23.2; 536/24.5; 435/6; 435/91.31; 435/172.1
[58] Field of Search ............... 435/6, 172.1, 91.31; 514/44; 536/23.1, 23.2, 24.5

[56] References Cited

FOREIGN PATENT DOCUMENTS

| 0387775 | 3/1990 | European Pat. Off. . |
| 9103162 | 3/1991 | WIPO . |

OTHER PUBLICATIONS

Weiss et al., Gene 111:183 (1992).
Medicine Abstract 90060615.
Medline Abstract 00286389.
Taylor et al. Cell. Biochem. J. Suppl. 15D, 1991 p. 21,CD 217.
Rossi et al. Cell. Biochem. J. Suppl. 15D, 1991, pp. 374, D 429.
Rossi et al. Cell. Biochem J. Suppl. 15D, 1991, p. 7, CD 011.
Ruffner et al. Biochem. v. 29, No. 47:10695 (1990).
PNAS 88:7303 (1991) Siond et al.
Johnson et al. Science 260:1286–1292, May 1993.
Barigana Science 262:1512–1514, Dec. 1993.
Biotechnolog Abstracts Acc #: 95–00442.
Goodchild Arch. Biochem Biophys. 284:386 (1991).
Hampel et al. NAR 18:299 (1990).
Sarver et al. Science 247:1222 (1990).
Barat et al. EMBO J. 8:3279 (1989).
Wolfgang et al Science 253:314 (1991).

*Primary Examiner*—John L. LeGuyader
*Attorney, Agent, or Firm*—Rothwell, Figg, Ernst & Kurz

[57] ABSTRACT

The invention provides novel chimeric tRNA$^{LYS}$-ribozyme molecules that compete effectively with tRNA$^{LYS}$ for HIV-1 reverse transcriptase binding sites. The chimeric human tRNA$^{LYS}$-ribozymes inhibit reverse HIV transcription by delivering inhibitors such as ribozymes of HIV-1 reverse transcriptase directly to the virion particle and render it non-functional. The chimeric molecules of the invention thus serve as highly specific non-toxic therapeutic agents. These chimeric molecules also reveal a novel, site specific RNA cleaving activity of HIV-1.

19 Claims, 3 Drawing Sheets

CHIMERIC TRNA$^{LYS}$-RIBOZYME MOLECULES

This invention was made with government support under Grant No. AT 25959 awarded by the National Institutes of Health. The government has certain rights in the invention.

FIELD OF THE INVENTION

This invention relates to chimeric tRNA$^{LYS}$ ribozyme molecules which compete effectively with tRNA$^{LYS}$ for binding to HIV-1 reverse transcriptase. These chimeric molecules provide a mechanism for delivering inhibitors of HIV-1 transcriptase to the virion particle itself.

BACKGROUND OF THE INVENTION

It has been demonstrated that the entire tRNA$^{LYS}$ molecule as well as various segments of the tRNA per se are capable specifically of interacting with HIV-1 transcriptase. See Barat, et al. *EMBO Journal* 8:3279–3285 (1989); Khan, et al. *J. Bio. Chem* 267:6689–6695 (1992); Weiss, et al., *Gene* 111:183–197 (1992). Ben-Artzi, *Proc. Natl. Acad. Soc. USA* 89:927–931 (1992) reports an RNAse cleavage activity associated with HIV-1 reverse transcriptase. This activity is shown to cleave only HIV-1 RNA, not the primer.

Prior to this invention there has been no report of chimeric tRNA$^{LYS}$-ribozyme molecules.

SUMMARY OF THE INVENTION

This invention provides novel chimeric tRNA$^{LYS}$-ribozyme molecules that compete effectively with tRNA$^{LYS}$ for HIV-1 reverse transcriptase binding sites. The chimeric human tRNA$^{LYS}$-ribozymes inhibit reverse HIV transcription by delivering inhibitors such as ribozymes of HIV-1 reverse transcriptase directly to the virion particle and render it non-functional. The chimeric molecules of this invention thus serve as highly specific non-toxic therapeutic agents.

These chimeric molecules also reveal a novel, site specific RNA cleaving activity of HIV-1.

EXAMPLES AND DESCRIPTION OF THE FIGURES

FIG. 1 shows the structure of one chimeric ribozyme. This tRNA$^{LYS}$-ribozyme construct has been cloned into a Blue Script transcription vector using SacII and XhoI restriction sites. Following linearization at the SacII site the chimeric RNA can be transcribed in vitro using bacteriophage T-7 RNA polymerase. There is also a Mae I restriction site in between the tRNA and ribozyme moieties, allowing the tRNA to be transcribed independently of the ribozyme.

Figure 2:
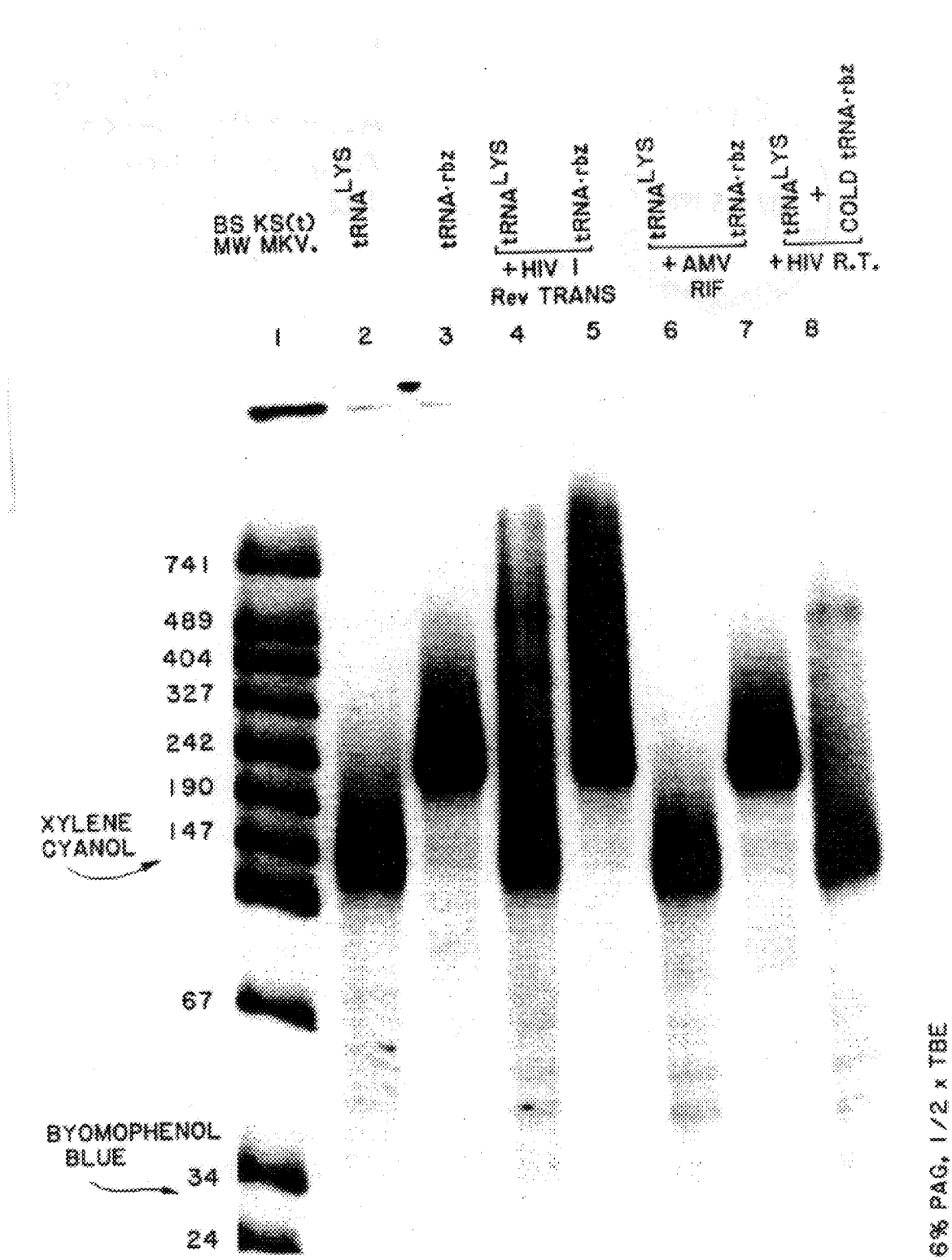

FIG. 2. This gel shift experiment shows binding of the chimeric tRNA$^{LYS}$-ribozyme to HIV-1 reveres transcriptase. The eight lanes of the gel from left to right are:

1. Molecular weight marker;
2. tRNA$^{LYS}$ in vitro transcript which has extra bases at both the 5' and 3' ends. The extra 5' bases are from the Blue Script poly linker between the T-7 promoter and the XhoI site. There are six extra nucleotides at the 3' derived from the nucleotides after the CCA of the tRNA to the Mae I site which separates the tRNA from the ribozyme.
3. tRNA$^{LYS}$-ribozyme in vitro transcript which has the same extra 5' bases as tRNA$^{LYS}$, but terminates at SacII site at the end of the ribozyme moiety.
4. tRNA$^{LYS}$ transcript incubated with HIV-1 reverse transcriptase.
5. tRNA$^{LYS}$-ribozyme transcript incubated with HIV-1 reverse transcriptase.
6. tRNA$^{LYS}$ transcript incubated with AMV reverse transcriptase.
7. tRNA$^{LYS}$-ribozyme incubated with AMV reverse transcriptase.
8. tRNA$^{LYS}$ with competing, non-radioactively labelled tRNA$^{LYS}$-ribozyme incubated with HIV-1 reverse transcriptase.

This FIG. 2 shows that the chimeric tRNA$^{LYS}$-ribozyme specifically binds to HIV-1 reverse transcriptase by a shift in radioactivity when HIV-1 reverse transcriptase is present. Cold tRNA$^{LYS}$-ribozyme competes with tRNA$^{LYS}$ for binding to HIV-1 reverse transcriptase as indicated by the reduced radioactive shift in lane 8.

Figure 3:
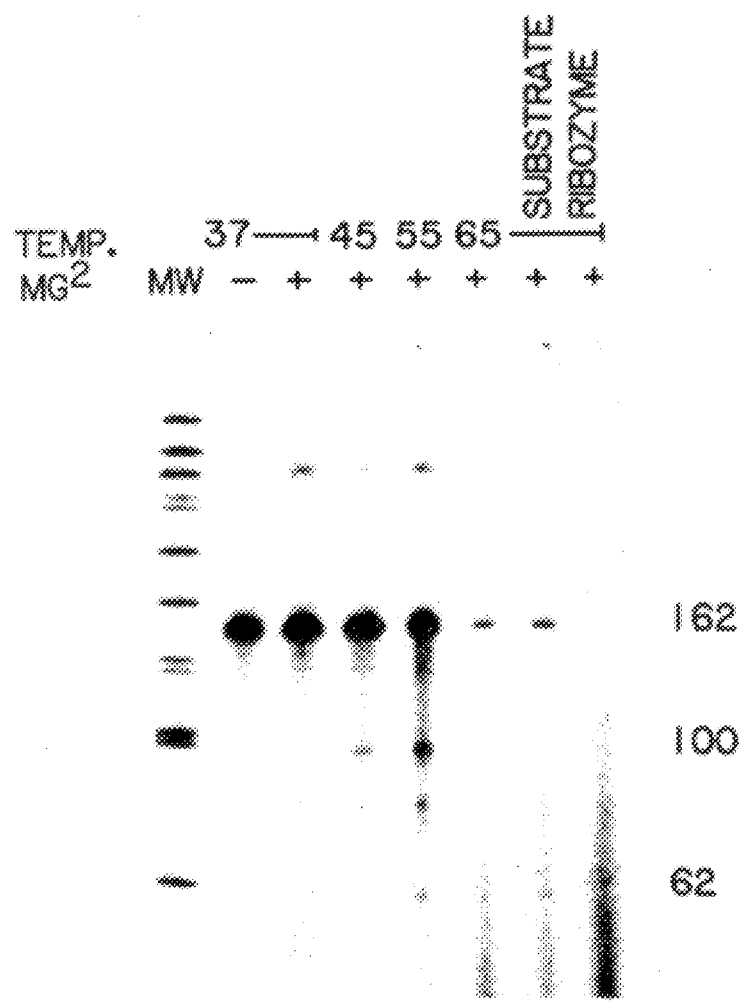

FIG. 3. This experiment demonstrates cleavage of a 162 nucleotide, radioactively labelled HIV-1 RNA containing the primer binding site plus sequences upstream of this and including the AUC cleavage signal for the ribozyme. The cleavage products are 101 and 61 bases. The extent of cleavage increases with increasing temperature.

GENERAL DESCRIPTION OF THE INVENTION

Genetic fusions consisting of the entire mature coding sequence or 18 bases of the 3' end of human tRNA$^{LYS}$ have been fused to hammerhead ribozyme containing RNAs with base pairing capabilities to the HIV-1 sequences immediately 5' or upstream of the primer binding site. The 3' terminal 18 nucleotides of the tRNA$^{LYS}$ are complementary to the primer binding site.

These chimeric molecules have been tested in cell free assays for their ability to bind to HIV-1 reverse transcriptase and their inhibitory activity on HIV-1 reverse transcriptase polymerization activity. The ribozyme moiety targets the cleavage of HIV-1 viral RNA at a known hammerhead cleavage site immediately upstream of the primer binding site for initiation of reverse transcription in the HIV-1 viral RNA. The site chosen for initial study, and reported here is an AUC in which cleavage is immediately after the C. This site is absolutely conserved in all HIV-1 isolates sequenced to date. The chimeric RNAs, which are specifically bound by HIV-1 reverse transcriptase should be carried into newly formed HIV-1 virions during viral assembly. The chimeric primers effectively block HIV-1 reverse transcription, making them a novel, highly target specific, and unique anti-HIV-1 therapeutic agent. In addition, the tRNA$^{LYS}$ portion contains within its mature coding sequence the elements required for transcription by human RNA polymerase III, thereby making it feasible to insert the gene, rather than the RNA into human cells.

Studies of the binding of the chimeric molecules to HIV-1 reverse transcriptase, revealed that the complex of chimeric tRNA$^{LYS}$-ribozyme, or 18 3' nucleotides of tRNA$^{LYS}$-ribozyme, or tRNA$^{LYS}$ with an extra 6 nucleotides appended to the 3' end, when base paired to the primer binding site signal of HIV-1 RNA, serves as a substrate for a novel ribonuclease activity associated with HIV-1 reverse transcriptase. This activity results in cleavage of the primer at a site very close to the 3' end of the tRNA$^{LYS}$ molecule, CCA-3'. This activity is of unknown function in the viral replication cycle, but may play an important role in the use of chimeric RNAs by freeing the ribozyme moiety from the tRNA moiety such that it can cleave one or both of the viral RNAs encapsidated in the HIV-1 virion.

GENERAL PURPOSE OR UTILITY OF THE INVENTION

The idea of chimeric tRNA$^{LYS}$-ribozyme molecules which effectively compete with tRNA$^{LYS}$ for binding to HIV-1 reverse transcriptase is novel. It provides a possible mechanism for specifically delivering inhibitors of HIV-1 reverse transcriptase to the virion particle itself. Such inhibitory agents will render these viral particles non-functional, and thus serve as highly specific, non-toxic therapeutic agents.

It has been demonstrated that the entire tRNA$^{LYS}$ molecule, as well as various segments of the tRNA itself are capable of specifically interacting with HIV-1 reverse transcriptase. No one has shown that chimeric molecules such as the the ones described could specifically bind to HIV-1 reverse transcriptase. No other work has described that such molecules are inhibitory to HIV-1 reverse transcriptase polymerase activity. There is one published report of an RNAse cleavage activity associated with HIV-1 reverse transcriptase. This activity was only shown to cleave HIV-1 RNA, not the primer. This activity cleaves twice in the primer binding site, and only substrates paired with tRNA$^{LYS}$.

The RNA attached to the 3' end of the tRNA$^{LYS}$ need not be a ribozyme, but any extra RNA which can base pair with the HIV-1 target upstream of the primer biding site. If a ribozyme is joined to the tRNA, other cleavage sites such as CUC, or CUA which are on the HIV-1 sequence just to the 3' side (downstream) of the AUC site can be targeted. It is not necessary to make an entire tRNA$^{LYS}$-ribozyme fusion because it is now known that the last 18 nucleotides of tRNA$^{LYS}$ fused to the ribozyme are also bound by HIV-1 reverse transcriptase. Genetic variants of tRNA$^{LYS}$ which compete better than tRNA$^{LYS}$ for binding to HIV-1 transcriptase are included in the invention.

The ribozyme fusions to tRNA$^{LYS}$ allow specific targeting of the ribozyme to the HIV-1 virion. Since all retroviruses use cellular tRNAs for priming, this invention provides a general strategy for inhibiting other retroviruses as well.

Existing ribozyme technology makes use of specific base pairing between ribozyme and target, but this is accomplished by diffusion of the ribozyme until it finds a target RNA. This invention uses well known retroviral packaging pathways to specifically carry the ribozyme into the virion, and get it bound to the correct site on the viral RNA for cleavage.

We claim:

1. A chimeric tRNA$^{LYS}$-ribozyme.

2. A chimeric human tRNA$^{LYS}$-ribozyme.

3. A construct comprising a ribozyme fused to a coding sequence of the 3' end of tRNA$^{LYS}$, said coding sequence being capable of base pairing with an HIV-1 viral RNA sequence.

4. The construct according to claim 3, wherein said tRNA$^{LYS}$ is human tRNA$^{LYS}$.

5. The construct according to claim 3 wherein said ribozyme is a hammerhead ribozyme.

6. The construct according to claim 4 wherein said ribozyme is a hammerhead ribozyme.

7. A complex as depicted by FIG. 1, wherein SEQ ID NO. 1 specifies the HIV-1 mRNA of FIG. 1 and SEQ ID NO. 2 specifies the tRNA$^{LYS}$-ribozyme construct of FIG. 1.

8. A molecule comprising at least the eighteen bases of the 3' end of tRNA$^{LYS}$ fused to a ribozyme moiety, said ribozyme moiety having an RNA sequence which base pairs with an HIV-1 viral RNA sequence immediately 5' of the primer binding site for initiation of reverse transcription in HIV-1 viral RNA, said ribozyme moiety being selected to target a cleavage site of said RNA sequence immediately 5' of the said primer binding site for initiation of reverse transcription in HIV-1 viral RNA.

9. The molecule according to claim 8, wherein said tRNA$^{LYS}$ is human tRNA$^{LYS}$.

10. The molecule according to claim 8, wherein said ribozyme moiety is a hammerhead ribozyme moiety.

11. The molecule according to claim 9, wherein said ribozyme moiety is a hammerhead ribozyme moiety.

12. A complex comprising HIV-1 reverse transcriptase bound to a chimeric tRNA$^{LYS}$-ribozyme, said chimeric tRNA$^{LYS}$-ribozyme comprising a tRNA$^{LYS}$ moiety and a ribozyme moiety, wherein the ribozyme moiety is capable of base pairing with an HIV-1 viral RNA sequence immediately 5' of the primer binding site for initiation of reverse transcription.

13. The complex according to claim 12, wherein said tRNA$^{LYS}$ moiety is human tRNA$^{LYS}$ moiety.

14. The complex according to claim 12, wherein said ribozyme moiety is a hammerhead ribozyme moiety.

15. The complex according to claim 13, wherein said ribozyme moiety is a hammerhead ribozyme moiety.

16. A nucleic acid complex comprising HIV-1 viral RNA bound to a chimeric tRNA$^{LYS}$-ribozyme, said chimeric tRNA$^{LYS}$-ribozyme comprising a tRNA$^{LYS}$ moiety and a ribozyme moiety, wherein said tRNA moiety is bound to a primer binding site for initiation of reverse transcription of the HIV-1 viral RNA.

17. The nucleic acid complex according to claim 16, wherein said tRNA$^{LYS}$ moiety is a human tRNA$^{LYS}$ moiety.

18. The nucleic acid complex according to claim 16, wherein said ribozyme moiety is a hammerhead ribozyme moiety.

19. The nucleic acid complex according to claim 17, wherein said ribozyme moiety is a hammerhead ribozyme moiety.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 35
( B ) TYPE: Nucleotides
( C ) STRANDEDNESS: Single
( D ) TOPOLOGY: Unknown ( i x ) SEQUENCE DESCRIPTION: SEQ ID NO: 1:

| | | | |
|---|---|---|---|
| UGGAAAAUCU | CUAGCAGUGG | CGCCCGAACA | GGGAC | 3 5 |

( 2 ) INFORMATION FOR SEQ ID NO: 2:

( i ) SEQUENCE CHARACTERISTICS:
( A ) LENGTH: 130
( B ) TYPE: Nucleotides
( C ) STRANDEDNESS: Single
( D ) TOPOLOGY: Unknown ( i x ) SEQUENCE DESCRIPTION: SEQ ID NO: 2:

| | | | | |
|---|---|---|---|---|
| GGCGCCUUUU | UACCGUUUAA | AGCAGGAGUG | CCUGAGUAGU | CAGAUCGUCA | 5 0 |
| CCGCGGGCUU | GUCCCUGAAC | UUGGGACCUG | GGAGUCUAAU | UUUCAGACUA | 1 0 0 |
| CGAGAUGGCU | GACUCGAUAG | GCCCGAGCUC | | | 1 3 0 |